United States Patent
Arnheiter et al.

(10) Patent No.: US 10,530,901 B1
(45) Date of Patent: Jan. 7, 2020

(54) DATA PROCESSING SYSTEM WITH TRANSLATOR FOR DIFFERENT MESSAGING PROTOCOLS

(71) Applicants: Matthew Arnheiter, Minneapolis, MN (US); Michael Brand, Farmingville, NY (US)

(72) Inventors: Matthew Arnheiter, Minneapolis, MN (US); Michael Brand, Farmingville, NY (US)

(73) Assignee: NETSMART TECHNOLOGIES, INC., Overland Park, KS (US)

( * ) Notice: Subject to any disclaimer, the term of this patent is extended or adjusted under 35 U.S.C. 154(b) by 947 days.

(21) Appl. No.: 14/990,454

(22) Filed: Jan. 7, 2016

Related U.S. Application Data (63) Continuation of application No. 12/924,564, filed on Sep. 28, 2010, now abandoned.

(60) Provisional application No. 61/278,062, filed on Oct. 2, 2009.

(51) Int. Cl.
*H04L 29/06* (2006.01)
*G16H 10/60* (2018.01)

(52) U.S. Cl.
CPC ............. *H04L 69/08* (2013.01); *G16H 10/60* (2018.01)

(58) Field of Classification Search
CPC ................................................ G06Q 50/22–24
See application file for complete search history.

(56) References Cited

U.S. PATENT DOCUMENTS

| | | | |
|---|---|---|---|
| 6,263,330 B1* | 7/2001 | Bessette | G06Q 50/22 |
| 7,653,634 B2* | 1/2010 | Mathur | G06F 21/6245 707/999.01 |
| 2003/0187689 A1* | 10/2003 | Barnes | G06Q 50/22 705/2 |
| 2005/0021376 A1* | 1/2005 | Zaleski | G06F 19/3418 705/3 |
| 2007/0210917 A1* | 9/2007 | Collins, Jr. | A61B 5/1117 340/539.1 |
| 2008/0046292 A1* | 2/2008 | Myers | G06Q 50/24 705/3 |
| 2008/0052113 A1* | 2/2008 | Cauley | G06F 19/328 705/2 |
| 2008/0140454 A1* | 6/2008 | Hernandez | G06F 19/321 705/3 |
| 2008/0140723 A1* | 6/2008 | Hernandez | G06F 19/321 |
| 2008/0215627 A1* | 9/2008 | Higgins | G06Q 10/06 |
| 2009/0006134 A1* | 1/2009 | Heidenreich | G06Q 10/00 705/3 |
| 2009/0063183 A1* | 3/2009 | McNeely | A61G 12/00 705/2 |
| 2009/0281833 A1* | 11/2009 | Boppana | G06Q 50/22 705/3 |

(Continued)

*Primary Examiner* — Robert A Sorey
(74) *Attorney, Agent, or Firm* — Stinson LLP (57) ABSTRACT

A health information exchange responds to providers' health document requests by directly accessing sources of those documents, thereby providing the requesters with more up-to-date health documents than may be available from a conventional health information exchange. The health information exchange of the invention is particularly advantageous in, although not limited to, the exchange of health documents in the behavioral-health or other medical fields where chronic conditions are treated and where patient information is frequently changed and/or augmented.

14 Claims, 8 Drawing Sheets

(56) References Cited

U.S. PATENT DOCUMENTS

| | | | | |
|---|---|---|---|---|
| 2010/0054142 A1* | 3/2010 | Moiso | .................. | H04L 67/327 |
| | | | | 370/252 |
| 2010/0131298 A1* | 5/2010 | Buttner | ................. | G06Q 10/10 |
| | | | | 705/3 |

* cited by examiner

| PATIENT RECORD | |
|---|---|
| FIELD | VALUE |
| FIRST NAME | JOHN |
| MIDDLE NAME | QUINCY |
| LAST NAME | DOE |
| DOB | 05-18-1947 |
| SSN | 047-48-3667 |
| GENDER | MALE |
| PROVIDER A ID | PT12677 |
| PROVIDER B ID | RTX-54-994 |
| PROVIDER M ID | 047-48-3667 |
| CONSENTS | HOSPITALS |
| ⋮ | ⋮ |

DATA PROCESSING SYSTEM WITH TRANSLATOR FOR DIFFERENT MESSAGING PROTOCOLS

CROSS-REFERENCE TO RELATED APPLICATIONS

This application claims priority to and is a continuation of U.S. patent application Ser. No. 12/924,564, filed on Sep. 28, 2010, which claims the benefit of U.S. Provisional Patent Application Ser. No. 61/278,062, filed on Oct. 2, 2009, each of which is incorporated herein by reference in its entirety.

BACKGROUND

The present invention relates generally to electronic medical record systems and, more particularly, to a known type of system—referred to as a 'health information exchange"—via which electronic medical record systems can share information.

Electronic medical record systems offered by a variety of vendors are used by hospitals, physicians' offices, laboratories, and other health-care-related facilities to store and retrieve in electronic form information pertaining to their patients. Such information may be in the form of patient identification data; various kinds of industry standardized electronic records such as CCDs (continuity-of-care documents), CCRs (continuity of care records) and CDAs (Clinical Document Architecture) documents; written textual material such as progress notes and discharge summaries; laboratory test results; and images such as X-rays and MRI scans, to name some of the most common. Each separately accessible datum or collection of data is referred to herein as a "health document." (In this specification and/or the claims hereof, the term "health information" is used to encompass both health documents per se and/or lists that identify (e.g., by title, date, etc.) one or more health documents, as will be apparent from the context.)

A health information exchange allows electronic medical record systems to share their health documents with one another. In operation, electronic medical record systems whose owners subscribe to a particular health information exchange upload individual patient's health documents into an electronic document repository maintained by the health information exchange. The information can be later retrieved by other health information exchange subscribers, enabling, for example, a presenting patient's healthcare provider (e.g., hospital) to readily obtain health documents that were created elsewhere (e.g., the office of the patient's primary care physician).

SUMMARY

In accordance with the present invention, a health information exchange is provided with the ability to obtain health documents from a source electronic medical record system directly, as opposed to obtaining them from a health document repository. We refer to our inventive approach as the "direct access paradigm," as contrasted with the prior art's "central repository paradigm."

The prior art's central repository paradigm works well in many situations, which is why it is still the exclusive model on the health information exchange landscape. Indeed, the prior art's central repository paradigm is in some ways better than our direct access paradigm. For example, our direct access approach may be slightly slower to return information since it introduces an additional link in the communication chain. Moreover, direct access to a source provider's electronic medical record system is contingent upon that system being "up" and "on line."

That having been said, our approach overcomes a number of drawbacks inherent in the central repository paradigm—drawbacks that we have come to recognize based on our unique perspective as designers of electronic medical record systems for the behavioral health field. Among the advantages of our approach is the providing of health documents that in at least some cases will be more up-to-date than are provided by conventional health information exchanges; a more efficient use of resources; enhanced control for providers over health documents that they create; and enhanced patient control by patients over health documents relating to them specifically.

Particular implementations of a health information exchange implementing the principles of the invention may incorporate a central repository paradigm in addition to implementing our direct access approach and may also access other health information exchanges' document repositories when a patient's health documents are requested. This, advantageously, enables a requester to obtain health documents created by a given patient's provider(s) who subscribe only to other health information exchanges.

DETAILED DESCRIPTION OF ILLUSTRATIVE EMBODIMENTS

Network Overview

Figure 1:
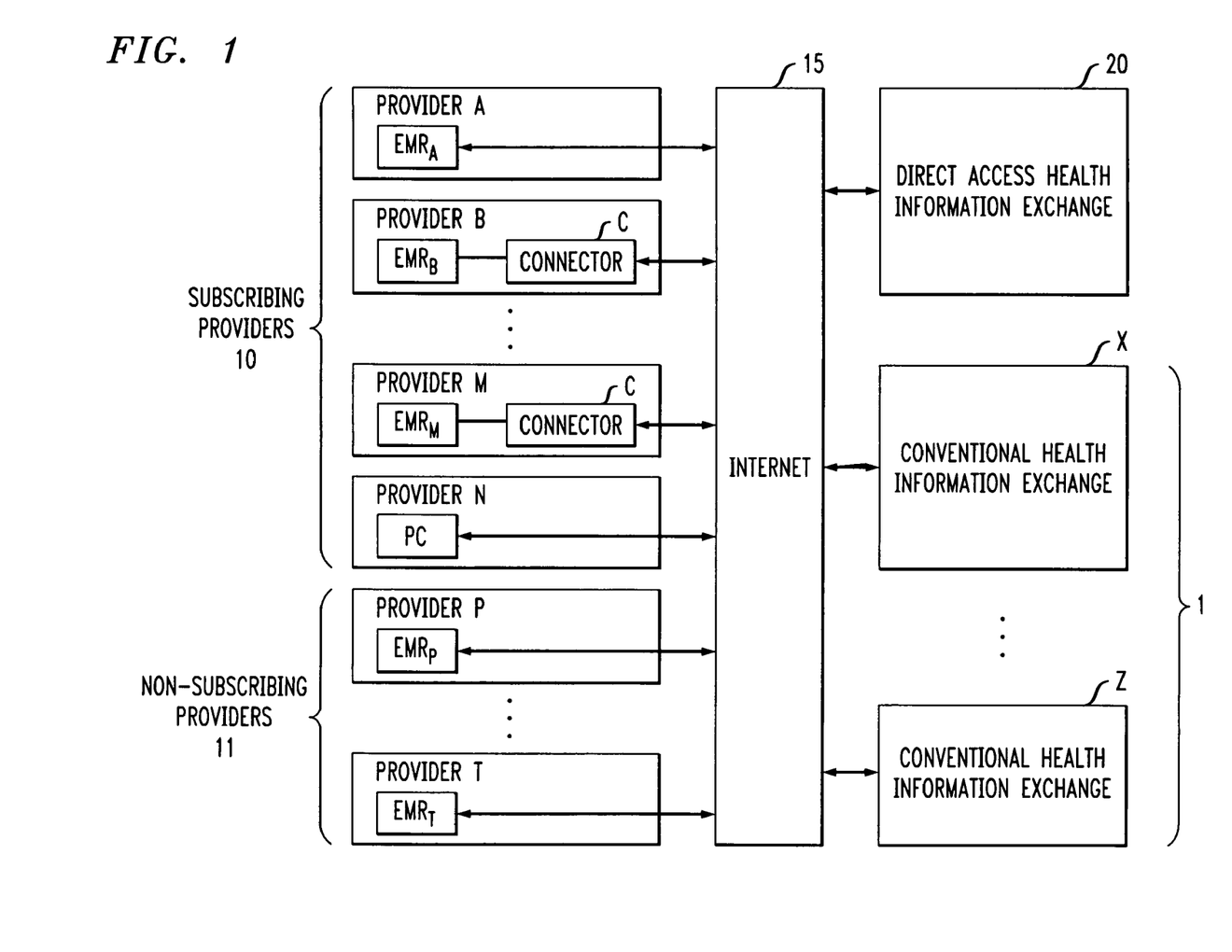
FIG. 1 is an overview of a health information network that includes a direct access health information exchange embodying the principles of the present invention.

The health information network of FIG. 1 includes subscribing providers 10, non-subscribing providers 11, conventional health information exchanges 12 and "direct access" health information exchange 20, which implements the principles of the present invention.

Subscribing providers 10 are subscribers of at least health information exchange 20 and may also be subscribers to one or more of health information exchanges 12. Non-subscribing providers 11 are also subscribers to one or more of health information exchanges 12, but are not subscribers to health information exchange 20. The providers' electronic medical record systems and health information exchanges communicate with one another over a wide area network—illustratively the Internet 15.

Subscribing providers 10 comprise individual providers A through N. Of these, providers A through M own and/or control electronic medical record systems $EMR_A$ through $EMR_M$, which may be on their premises. Among providers A through N may be hospitals, physician's offices, medical testing laboratories, etc. (The term "provider" is used herein to encompass all types of entities that subscribe to one or more of the health information exchanges, whether or not they are health care providers, per se.)

A certain number of the providers A through M are large institutions, such as hospitals, whose electronic medical record systems are high-powered, feature-rich systems installed on dedicated servers and tailored by the system vendor to meet the institutions' specific needs. An example is the Avatar® system offered by Netsmart Technologies, Inc. Others of those providers are smaller entities, such as individual physician's offices, medical laboratories, etc., whose electronic medical record systems are implemented by so-called shrink-wrap, or commercial off-the-shelf (COTS), software applications that have limited capabilities and are typically installed on office computers alongside other stand-alone software packages that may be in use at the facility in question.

One or more of electronic medical record systems $EMR_A$ through $EMR_M$—as represented by electronic medical record system $EMR_A$ has the native ability to communicate with health information exchange 20 using the same messaging protocol as health information exchange 20. For example, electronic medical record system $EMR_A$ and health information exchange 20 may be offered by the same vendor which has programmed them to utilize a particular messaging protocol designed by that vendor.

By contrast, one or more of the other electronic medical record systems, as represented by systems $EMR_B$ through $EMR_M$, do not have the native ability to communicate with health information exchange 20. Specifically, different vendors' electronic medical record systems typically use a particular industry-standard or proprietary messaging protocol when communicating with other systems and those vendors may not be willing to provide their systems with the ability to use health information exchange 20's protocol nor may they be willing, or even able, to retrofit systems that are controlled by providers and/or deployed on provider premises—particularly in the case of COTS systems.

However, each of systems $EMR_B$ through $EMR_M$ has an associated computer system, referred to as a "Connector," described in detail hereinbelow. For the present it suffices to note that the Connector serves to translate between the messaging format of the protocol used by health information exchange 20 and the messaging format(s) used by the associated ones of the electronic medical record systems $EMR_B$ through $EMR_M$. Thus a provider may have a non-compatible electronic medical record system and yet be able to communicate to one of health information exchange 20's subscribing providers.

Subscribing provider N is illustratively a small entity that, as noted above, does not have an electronic medical record system. However, provider N is nonetheless able to avail itself of at least some of the services of health information exchange 20 via a web interface accessed through a web browser installed on a personal computer PC, as discussed more fully below.

Non-subscribing providers 11 comprise providers P through T having medical record systems EMIR through $EMR_T$. Providers P through T are not subscribers to health information exchange 20. They are, rather, subscribers to one or more of the traditional, document-repository-based health information exchanges 12.

The Direct Access Paradigm

Let us first consider a typical prior art scenario involving one of the conventional health information exchanges 12. In this scenario, John Doe is a behavioral health patient at Provider P, which is a mental health clinic. John has a psychotic episode triggered by a recent change in medication and is brought in the middle of the night to Provider T, which is a hospital emergency room. Provider P is a subscriber to health information exchange Z and John had previously given his consent for his records to be uploaded and stored in health information exchange Z. For whatever reason, information about the new medication was never uploaded into health information exchange Z and so hospital personnel at Provider T, in accessing whatever information about John is available at health information exchange Z, do not find this crucial piece of information, which would certainly be of value in determining the reason for John's presenting behavior.

Now let us assume a different scenario where John Doe is a behavioral health patient at a different mental health clinic—Provider A—and he arrives in the middle of the night at a different hospital emergency room—Provider B. Hospital personnel at Provider B cause their electronic medical record system $EMR_B$ to access health information exchange 20 to seek whatever information can be gotten about John. John is already known to health information exchange 20 because at the time he became a patient at Provider A, he gave his consent to have his medical information supplied to health information exchange 20. Provider A had thereupon supplied that information, along with the alphanumeric code used in electronic medical record system $EMR_A$ to identify John Doe, to health information exchange 20. Thus at the time that John shows up at Provider B, health information exchange 20 already knows that John is a patient at Provider A.

In this particular embodiment, health information exchange 20 has one or more central medical record repositories, as in the prior art, and can supply to Provider B whatever information may have been deposited within health information exchange 20 by Provider A and by any other one of providers 10 where John may have become a patient and given consent. However, unlike conventional health information exchanges 12, health information exchange 20 also implements the direct access paradigm of the present invention, wherein health information exchange 20 has the ability to obtain health documents from subscribing source electronic medical record systems directly—in this case Provider A. Thus, responsive to the request from Provider B, health information exchange 20 not only looks in its own document repository, but also queries the electronic medical record systems at each of providers 10 wherein John is a patient to obtain the most recent information that each of those providers has that pertains to John. Among those queried electronic medical record systems is $EMR_A$ which supplies to health information exchange 20 a document containing John's current medication information. Thus even if John's most recent medication records had not already been provided the health information exchange 20, as in the first case, personnel at Provider B is are made aware of John's current medication regime, including the recent change that, as it turns out, gave rise to the psychotic episode that brought him to Provider B's emergency room.

Advantages of the Direct Access Paradigm

The foregoing illustrates a significant advantage of the direct access paradigm of the present invention—namely the provision of more up-to-date health care documents than may be provided by a health information exchange operating under the central repository paradigm.

In particular, a health information exchange operating under the prior art's central repository paradigm can only provide such health documents as may have been posted to the repository as of the time of the request. A great number of electronic medical record systems are designed to upload new health documents only upon a patient's discharge or other treatment milestone—rather than upon the information being created. This is not a particular concern for scenarios for which health information exchanges were originally envisioned—namely the acute care scenario. Thus the central repository paradigm works fine in a case where a patient with, say, a broken limb gets treated by a particular provider and is ultimately discharged, at which point the provider's electronic medical record system uploads the patient's records to a health information exchange. If two years later the same patient presents to a different provider for any reason, the new provider can readily retrieve all of the records associated with the first incident and its treatment.

We have recognized, however, that the approach of uploading health documents to a health information exchange upon discharge or other treatment milestone is far from ideal when dealing with behavioral health or other chronic care models. Behavioral health patients, for example, may be treated with chronic mental illness and their medications may be frequently changed while the patient is still in active treatment. Yet with no treatment milestone, e.g., discharge, to trigger an upload to an health information exchange, providers requesting information from a health information exchange may not be afforded the most up-to-date information. By contrast, the direct access paradigm that informs the present invention—because it involves the obtaining of health documents from a provider in response to a real-time request for same from a subscriber—affords requesters with the opportunity to obtain the most up-to-date information extant, as we saw above in the case of John Doe.

Even if particular electronic medical record systems were to upload new or revised health documents immediately upon their creation or revision, there is no guarantee, and no ready way for a health information exchange to know, whether any particular electronic medical record system has provided its most recent health document(s) or not.

Another advantage of the present invention is resource efficiency. The central repository paradigm requires that the health information exchange have enough resources—particularly data storage capability—to receive and store mountains of data, even though most of it will never be of any interest to other health information exchange subscribers and, indeed, will never be requested by them. And while it might be possible in such a case for the health information exchange to aggregate those many pieces of health data into a single "view" of the patient, thereby reducing data storage requirements, the aggregation process may actually change the data in some way.

By contrast, a health information exchange embodying the direct access paradigm of the present invention can provide a requester with whatever information the requester would like while not involving such duplicative storage (nor the inaccuracies that can result from data aggregation). Avoidance of duplicative storage is of particular advantage for behavioral health or other chronic medical scenarios because of the large amount of data that is typically created in those settings—therapists' daily reports/notes, frequent medication adjustments, etc.

Yet another advantage of our health information exchange relates to provider control. Providers may not be willing—due to financial, policy, privacy or other concerns—to upload all of their records to a central repository not under their direct control. For example, a hospital may be reluctant to allow other hospitals—who are in some sense their competitors—to have access to the former's entire patient database. Such a provider may, however, be willing to respond to requests for the health documents pertaining to particular patients, per the direct access paradigm of the present invention.

Yet another advantage of our health information exchange relates to patient control. Even in the traditional health information exchange setting, patient consent is required before a provider can share with others health information pertaining to the patient, such as by uploading the information to a health information exchange. However, once a health care provider releases information to the typical health information exchange, control over who can access that data is determined by the health information exchange itself, with little if any further control on the part of the provider or patient.

By contrast, in a health information exchange embodying the principles of the invention, a patient can change her mind at any time by withdrawing her consent at the provider's office as to which, or what type, of requesting entities, if any, she is willing to receive her medical information. Upon processing a subsequent requester's request, our health information exchange will become aware of the fact that the patient has withdrawn her consent—this is information that is initially supplied, and later updatable, from the provider's system—and will reject the request. This is a particularly significant advantage in the behavioral health field in that patients are often more concerned with the privacy of their behavioral health documents than with other health categories of health data.

Particular implementations of a health information exchange implementing the principles of the invention may, in addition to implementing our direct access paradigm, also have an associated central repository in which the health information exchange can store all, or a portion, of the health documents that it had obtained from providers' electronic medical record systems. This makes the documents all the more readily available if additional requests are later made for the same documents and also allows for at least some of the health documents pertaining to a particular patient to be available in the event that the provider's electronic medical record system is off-line or otherwise not accessible at the time that a direct access request is made.

Health Information Exchange Architecture

Figure 2:
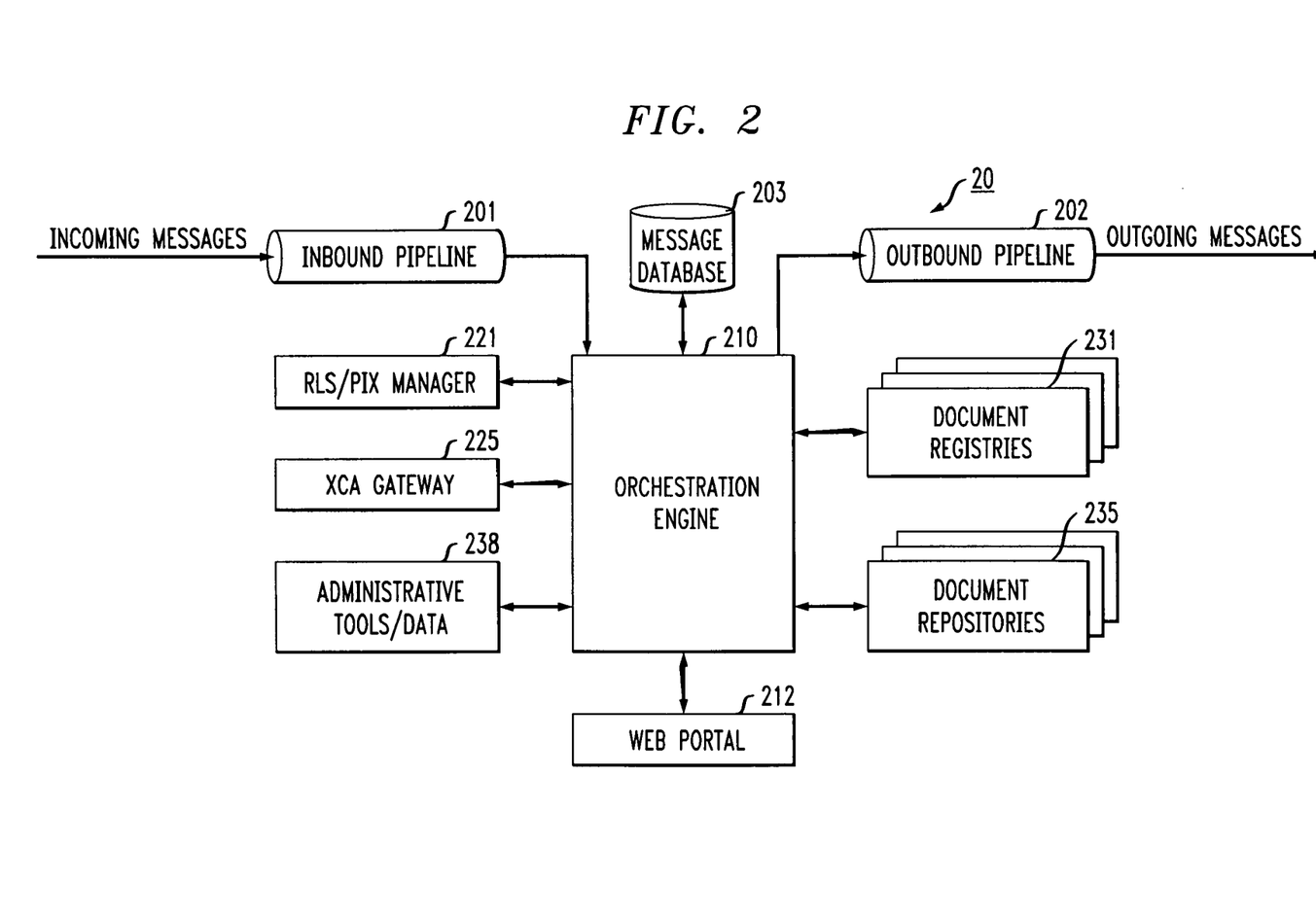
FIG. 2 is a conceptual block diagram of the health information exchange.

A conceptual block diagram of health information exchange 20 is shown in FIG. 2. Health information exchange 20 is illustratively implemented by a conventional Windows®-based web server—or a server using any other desired operating system—that has been programmed and configured in a straightforward manner that is within the capabilities of those skilled in the art, who will be able to implement the functionalities of health information exchange 20 as described herein.

The main components of health information exchange 20 are orchestration engine 210; record locator service/patient identifier cross-reference (RLS/PIX) manager 221; document repositories 235; document registries 231; inbound pipeline 201: outbound pipeline 202: message database 203; web portal 212; Cross-Community-Access, or XCA, gateway 225; and administrative tools/data 238, which will each now be discussed in turn.

Orchestration engine 210 is the central application software of health information exchange 20. It acts on received incoming messages and creates and transmits outgoing messages to thereby implement the overall functions of health information exchange 20 as described herein.

Orchestration engine 210 illustratively carries out two types of message processing scenarios.

One of these may be called "simple" process orchestration where the message processing flow proceeds from one step to the next without having to wait for external events. A typical example is where one of the providers where a particular patient is registered was requested to provide the latest health documents that they may have for that patient and one of the providers, a medical laboratory, is now responding with a lab test result. Health information exchange 20, upon receiving the test, forwards it on to the requesting subscriber.

The other type of message processing scenario may be called a "long running business transaction." A typical such transaction begins with a referral of a patient from one provider to another. For example, a psychiatrist's health patient has just decompensated and the psychiatrist wants to send the patient immediately to an inpatient mental health facility. In a situation like this, it is important for health information exchange 20 to keep the transaction "alive" until the electronic medical record system to which the referral is being made confirms that it has received the referral. This scenario is described in further detail hereinbelow in connection with the flowchart of FIG. 7. For the present it suffices to note that in order to support this kind of transaction, orchestration engine 210 will include, for example, persistence and state management software and other appropriate software that keeps track of the "state" for this transaction, e.g., "waiting for response from inpatient hospital," and takes appropriate action depending on further developments, e.g., notifies the requester that the referral was not even responded to.

RLS/PIX manager 221 is a database subsystem that keeps track of patients whose providers have registered them to the system. RLS/PIX manager 221 may thus include a database entry, shown in conceptual form in FIG. 3, for each registered patient. Illustratively, health information exchange system 20 keeps note of the various alphanumeric codes used by each provider to identify a given patient. In this example, then, Providers A, B and C identify the patient John Quincy Doe by the codes PT12677, RTX-54-994 and 047-48-3667, respectively.

Document repositories 235 is a document storage system comprising one or more document storage facilities (e.g., database systems) that may be a) co-located with the rest of health information exchange 20 and/or b) located on providers' premises, as explained more fully below. Document repositories 235 store health documents as they are received by health information exchange 20 from subscribing providers. Although the main focus of the present invention is health information exchange 20's ability to obtain health documents from a source electronic medical record system directly, as opposed to obtaining them only from a central health document repository, it is advantageous from a number of standpoints for health information exchange 20 to also maintain document repositories 235. For example, whenever health information exchange 20, per our direct access paradigm, a) receives a request for health information pertaining to a particular patient, b) goes out and gets such information from one or more electronic medical record systems, and c) provides it to the requester, health information exchange 20 also stores that information in document repositories 235. This enables health information exchange 20 to respond to subsequent requests for the same document without having to access the source electronic medical record a second time. It also enables health information exchange 20 to respond to requests for health documents if a particular provider's electronic medical record is off line or otherwise not accessible at a given time.

A further use of document repositories 235 is to serve as the main repository of health documents for those of the subscribers who may wish to use document repositories 235 as their long-term document storage mechanism by, for example, pushing data through an HL7 interface a periodic FTP upload from the subscriber's electronic medical record system to health information exchange 20. Or the subscriber may wish to use document repositories 235 as an off-site backup storage mechanism.

Another possibility is that a particular provider's electronic medical record system is not configured or operated in a way that enables it to provide health documents on demand pursuant to our direct access paradigm. Such providers and their patients may, however, be interested in allowing requesters to have access to their health documents. In this situation the provider's system might upload its health documents to document repositories 235 on a regularly scheduled or other basis.

There are several reasons that document repositories 235 may be desired to comprise multiple document storage facilities. The operator of health information exchange 20 may itself choose to have multiple such facilities at its central location or at satellite locations for various reasons such as speedier access, security, backup, etc. In addition, some subscribers may be willing to have their patient health documents stored where they can be accessed by health information exchange 20 but want to maintain physical control by having their health documents stored on their own premises. Thus one or more of the document storage facilities of document repositories 235 may exist within subscriber-premises facilities.

Health information exchange 20 enables subscribers to access the documents stored in the document storage facilities or repositories 235, either on their own premises or on the premises of health information exchange 20, either through their electronic medical record systems or web portal 212 (discussed below).

Document registries 231 is a database that keeps track of what documents are stored in document repositories 235 and in which of the storage facilities that comprise document repositories 235 any given document is stored. Each document is indexed by, for example, the associated patient's unique identifier for ready retrieval. Document registries 231 is actually representative of any number of document registries accessible and/or managed by health information exchange 20. For example, some providers may choose to have their health documents indexed only in a registry that is maintained on the providers' premises. This fact would be stored within administrative tools/data 238 so that orchestration engine 210 will know what registry to look in when seeking to obtain a stored document.

Inbound pipeline 201 processes incoming communications from the electronic medical record systems of Providers A through M, which are in the form of structured messages. Inbound pipeline 201 comprises a series of consecutively executed software modules that carry out such functions as determining the type of communication being received—for example, web service call, FTP file placement or email; decoding, disassembling and validating each message to authenticate the transmitting party and to determine that the message or request is of a recognized type; and other functions that those skilled in the art will recognize as being possibly desirable. The incoming message or request is thereupon taken over by orchestration engine 210 to carry out the appropriate workflow function(s), three of which are described below by way of example.

Outbound pipeline 202 performs the inverse functions of inbound pipeline 201—receiving from orchestration engine 210 output messages, which may include one or more health documents; packetizing them for transmission to an intended destination; providing appropriate authentication so that the receiving entity is assured that the communication is a bona fide message from health information exchange 20; and so forth.

Message database 203 stores a copy of all incoming and outgoing messages. Its principal function is to provide so-called stateful storage so that if, for example, the system were to crash, its state could be recovered.

Web portal 212 provides an alternative communications port for orchestration engine 210. This web portal enables subscribers to access health information exchange 20 through a conventional type of web browser interface and be availed of at least some of the health information exchange's features without the subscriber having to have a formal electronic medical record system. Additionally, a provider desiring to become a subscriber to health information exchange 20 can readily do so through the web portal 212. In the illustrative embodiment of FIG. 1, web portal 212 is the only means of access to health information exchange 20 by provider N.

XCA gateway 225 provides access to the conventional health information exchanges 12 shown in FIG. 1. Specifically, in responding to a request for health document(s) pertaining to a particular patient, health information exchange 20 may not only a) directly access electronic medical record systems where the patient is registered, in accordance with the invention, and b) provide documents that may have already been stored in document repositories 235, but may also request health documents from conventional health information exchanges 12, either directly or, when it becomes operative, via the Nationwide Health Information Network now under development. XCA gateway 225 implements a standardized protocol by which health information exchanges can communicate with, and exchange information among, one another. By specifying certain key patient-identifying information—first name, last name, gender, social security number and date of birth—health information exchange 20 is thus able to uniquely and accurately identify a particular patient to any given one of health information exchanges 12 that health information exchange 20 may have access to, and thereby obtain health documents that may be stored in one or more of health information exchanges 12 for that particular patient. Moreover, health information exchange 20 will specify to the other health information exchange(s) which entity is requesting information. This is necessary because access to data via a health information exchange is by way of pre-arrangement. That is, a health information exchange decides, based on their own policy considerations and possibly legal constraints, whether or not to release requested information to particular requesters.

Administrative tools/data 238 includes various utilities and information that those skilled in the art will recognize as being desirable based on the description herein and/or based on general principles of system design. Thus, for example, it is in administrative tools/data 238 where information about each of the subscribing providers resides. Such information would include, for example, the type (e.g., vendor and model number) of the electronic medical record system that is in place at a given provider, its Internet address, authentication passwords, etc. This and other administrative-type information is used by orchestration engine 210 to confirm the validity of requests and messages and to determine where outgoing messages are to be routed. It is also used in the course of mediating referral requests, as discussed below in conjunction with FIG. 7.

Other information in administrative tools/data 238 includes information about the document formats and coding that may be used in each subscribing electronic medical record system. For example, some systems may use HL7's CDA document standard, others the CCD standard, others the CCR standard, and so forth. Thus part of the processing performed by orchestration engine 210 is to determine from administrative tools/data 238 what standard a given requesting electronic medical record system uses and to convert incoming data to that form if it comes in in a different form. And at the coding, or data, level, a particular lab may use certain codes in its lab test reports but a requesting subscribing electronic medical record system may use different codes. Again, based on information in administrative tools/data 238, orchestration engine 210 can convert the coding of incoming data to comport to that used by the requester.

Messaging Protocol

Figure 8:
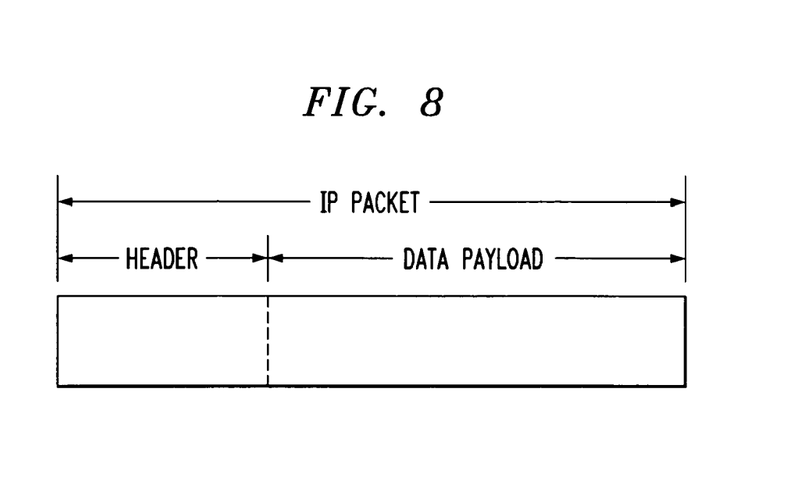
FIG. 8 shows the format of IP packets that convey messages and other information between the health information exchange and its subscribing providers.

Communications between health information exchange 20 and subscribing providers 10 are in the form of IP packets. As shown in FIG. 8, an IP packet comprises a header portion and a data payload portion. The format of the data payload portion is such as to implement a messaging protocol that enables health information exchange 20 to effectuate the functionalities described herein. The messaging protocol is thus an ISO level 7 (application layer) protocol and is thus analogous to any number of known "over-IP" protocols. So-called "voice-over-IP" is one example. Another example is an HL7-over-IP protocol by which some electronic medical record systems and health information exchanges exchange HL7 documents. As with all such "over-IP" protocols, the messaging protocol used by health information exchange 20 defines a number of fields within the data payload portion of the IP packet, as well as different message types. Given the desired functionality of health information exchange 20 as described herein, it is within the capability of those skilled in the art to straightforwardly design such a protocol including its various fields and its message set.

The protocol, including its message set, may be similar to and/or be a combination of, one or more of the known standards for message interchange. These include Health Level Seven Version 2.x promulgated by the standards-developing organization Health Level Seven (HL7) International; Health Level Seven Version 3 also promulgated by HL7 International; and/or the IHE (Integrating the Health Enterprise) Technical Framework which includes standards for Cross-Enterprise Document Reliable Interchange (XDR), Cross-Enterprise Sharing of Scanned Documents (XDS-SD), and Basic Patient Privacy Consents (BPPC). All of these standards are hereby incorporated by reference as if fully set forth herein. The message types that a particular embodiment of the invention may support will depend on what particular functionalities may be found find desirable or useful.

Connector

As noted above, electronic medical record systems offered by different vendors' electronic medical record systems use various different messaging protocols when communicating with other electronic medical record systems or with health information exchanges.

Electronic medical record system $EMR_A$, in particular, has been programmed to use the messaging protocol implemented by health information exchange 20. That is, electronic medical record system $EMR_A$ is able to use the message set and the formats that health information exchange 20 expects to see and that health information exchange 20 uses when transmitting communications back to the subscribing electronic medical record systems. Electronic medical record system $EMR_A$ and health information exchange 20 may be, for example, manufactured by the same vendor and thus will have been designed to communicate using that particular messaging protocol.

By contrast, electronic medical record systems $EMR_B$ through $EMR_M$ are not able, i.e., have not been programmed, to use the messaging protocol implemented by health information exchange 20. They may, for example, have been manufactured by various other vendors who may not be willing to provide their systems with the ability to use health information exchange 20's messaging protocol. Indeed, various ones of electronic medical record systems $EMR_B$ through $EMR_M$ may not be not able, i.e., may not have not been programmed, to use the messaging protocol implemented by conventional health information exchanges 12 either.

The prior art's solution to this issue is to provide centralized messaging protocol conversion. That is, the health information exchanges are designed to—and/or upgraded to be able to—receive and transmit health documents to and from its subscribing providers' electronic medical record systems using the messaging protocols that those various electronic medical record systems have been designed to operate with.

The present inventors have devised an alternative, which we refer to as a Connector, shown as Connector C in FIG. 1. As in the prior art centralized approach, Connector C serves to translate between a health information exchange's messaging protocol and the messaging protocol used by its subscribing electronic medical record systems $EMR_B$ through $EMR_M$.

However, instead of doing the translation centrally, our approach does it at the edges.

Specifically, an instantiation of Connector C is installed in association with each of the subscribing electronic medical record systems $EMR_B$ through $EMR_M$. The Connector C is illustratively a stand-alone server installed on a provider's premises behind its Internet firewall and translates between the messaging protocol utilized by the electronic medical record systems and health information exchange 20. To the extent that the provider's staff needs to manually interface with the Connector—as opposed to the provider's electronic medical record system's automatic response to the Connector to service document requests, for example—the Connector can present itself to the staff in the form of a browser-accessible website instantiated within the Connector C and accessible over the provider's local area network.

In this way, outgoing communications from an electronic medical record system to health information exchange 20 are converted from that electronic medical record system's messaging protocol to health information exchange 20's protocol and thereupon sent to health information exchange 20. Similarly, incoming messages to an electronic medical record system from health information exchange 20 are converted from health information exchange 20's protocol to the electronic medical record system's messaging protocol and thereupon presented to the electronic medical record system itself.

Our approach is counterintuitive because it would seem to be much more efficient to do the translation centrally, as in the prior art. We have recognized, however, that there are a number of advantages to performing the translation in a device, e.g., our Connector C, that is associated with each electronic medical record system.

One of those advantages relates specifically to the fact that health information exchange 20 implements the direct access paradigm of the present invention. Specifically, the practical effect of doing the translation centrally within a health information exchange is that a health information exchange implementing the direct access paradigm would then be making direct queries into the providers' database. We have recognized that providers are going to be reticent to allow some system somewhere out on the Internet to directly connect into their database in that way. They are going to be more willing, however, to allow a system (i.e., our Connector C) that is local to their system query their database and then the perform the translation.

And not only does Connector C provide standards-based connectivity software, but it enables real-time information sharing between any two systems, whether they are shrink-wrapped or enterprise.

Connector C can have the additional capability to accept from a provider's electronic medical record system—or from the provider's staff via the aforementioned local web-site—health data not already put into a standard healthcare document format and to put that data into such format, such as a CCD, CCR or CDA, for later retrieval in that form from, say, one of document repositories 235.

Figure 4:
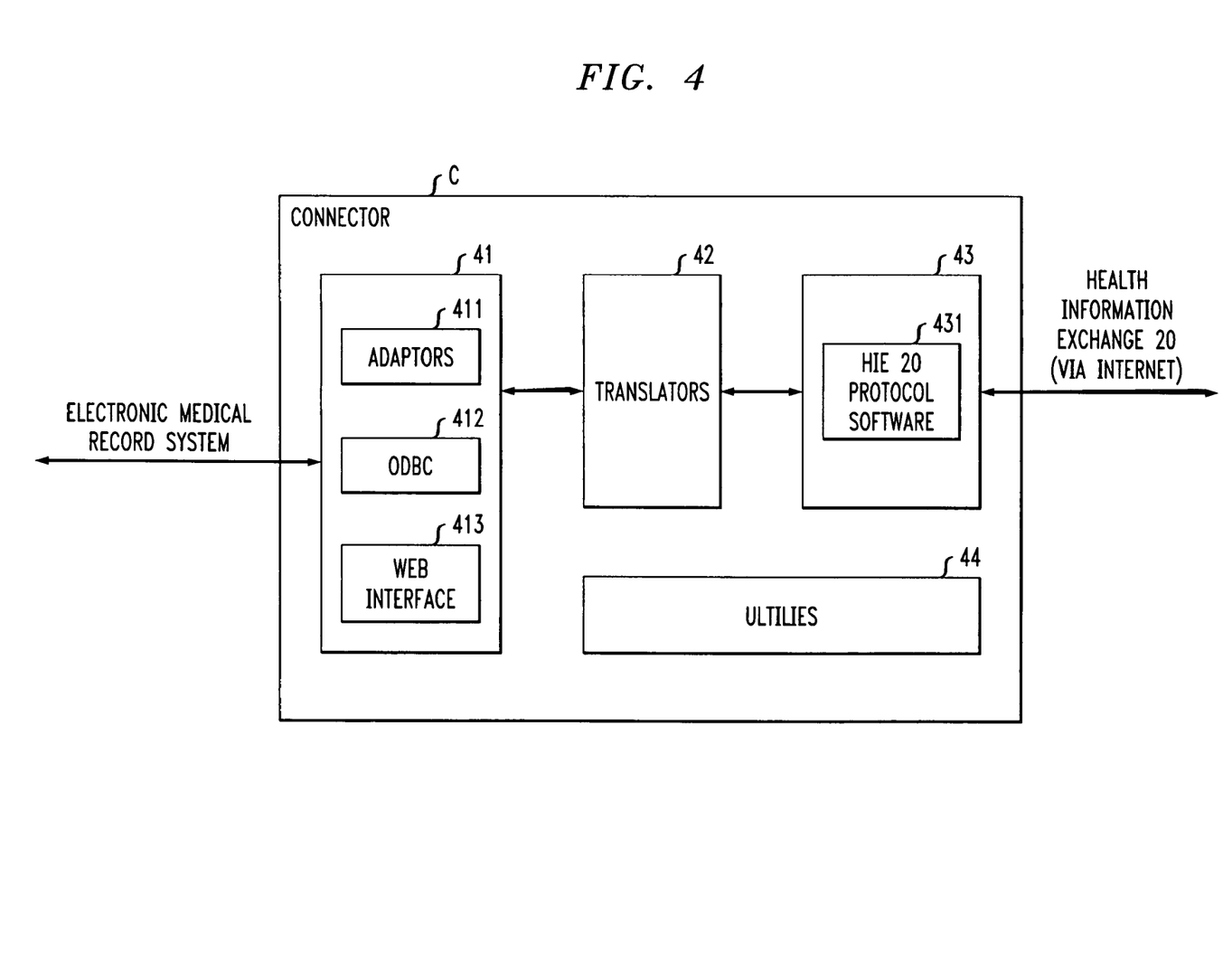
FIG. 4 is a conceptual view of a device that we refer to as a "Connector" that interfaces between the health information exchange and various electronic medical record systems.

FIG. 4 is a conceptual view Connector C, which is illustratively a standard server programmed to perform the functionalities discussed herein.

The basic functional blocks of interest for the present discussion are external interface 41, translators 42, internal interface 43 and utilities 44.

External interface 41 includes adaptors 411, ODBC interface 412 and web interface 413.

Adaptors 411 are software modules that are able to communicate with electronic medical record systems $EMR_B$ through $EMR_M$ using whichever of the messaging protocols is used by any particular one of the electronic medical record systems.

ODBC interface 412 is a standard software interface for accessing database management systems. It may turn out that a particular electronic medical record system, say $EMR_M$, may not have any capability, using any messaging protocol, to respond to the kinds of requests that may come from health information exchange 20. Thus, for example, electronic medical record system $EMR_M$ may not have the native ability to receive and respond to an external request for a health document. ODBC interface 412 is provided in such cases. It can respond to an appropriately translated incoming message from health information exchange 20 to directly access the internal database of electronic medical record system $EMR_M$ and retrieve the requested document.

Web interface 413 provides a human interface for providers' staffs, as mentioned above.

Internal interface 43 principally includes health information exchange 20 protocol software 431 that is able to communicate with health information exchange 20 using the latter's messaging protocol. Translators 42 translate, or convert, messages between protocols. Thus, for example, a "get document" type of message intended for electronic medical record system $EMR_B$ is sent by health information exchange 20 using the latter's messaging protocol. The message is received and acknowledged by protocol software 431 and is translated by translators 42 into a "get document" type of message as defined by the protocol used by electronic medical record system $EMR_B$. The translated message is passed to the appropriate one of adaptors 411 which thereupon communicates with electronic medical record system $EMR_B$ to obtain the document in question. Communications in the other direction are translated similarly.

Utilities 44 is a set of programs, files, databases, etc. that those in the art will recognize may be appropriate to implement the functions of Connector C as described herein. Thus utilities 44 specifically includes software for carrying out the above-mentioned function of formatting health data not already in a standard healthcare document form.

Workflows

Figure 5:
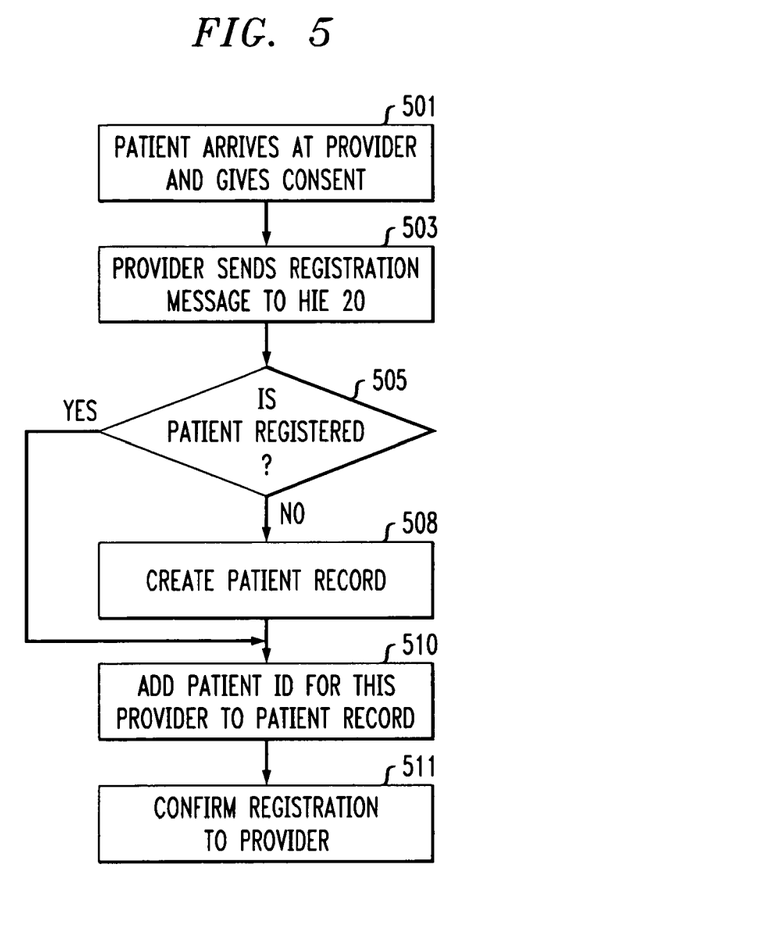
FIGS. 5-7 are flowcharts depicting illustrative workflows carried out by, and/or in cooperation with, the health information exchange to, respectively, a) register a new patient, b) process a request for a health document or a list of available health documents, and c) make a referral from one provider to another.
Figure 6:
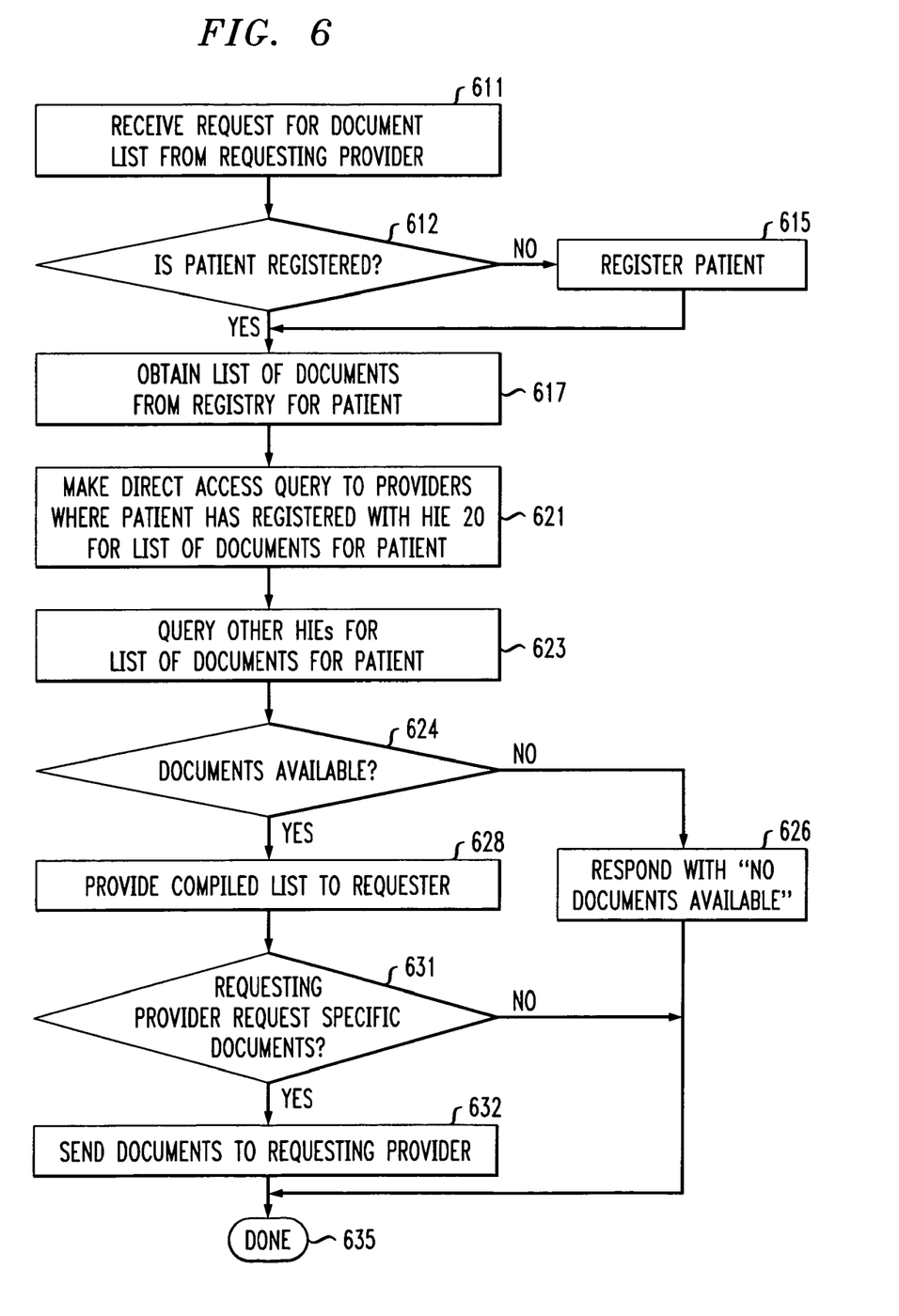
Figure 7:
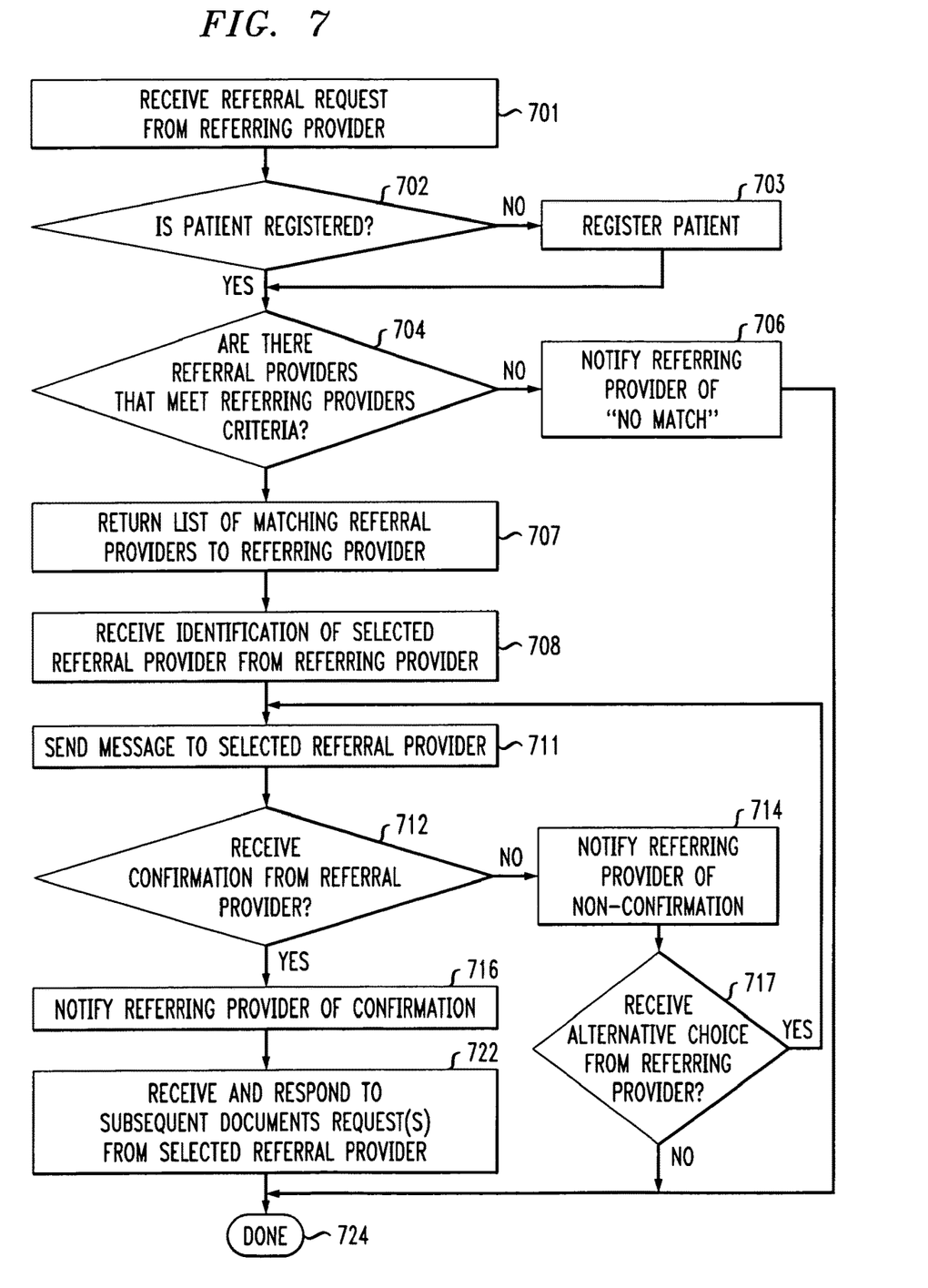

Flowcharts for three of the basic workflow processes carried out by health information exchange 20 are shown in FIGS. 5-7. Those skilled in the art will readily recognize and be able to design and implement these and other workflows that may be deemed desirable to implement the functionalities of health information exchange 20 as described herein.

The workflow of FIG. 5 is an illustrative process by which a patient becomes registered at health information exchange 20.

As indicated at 501, the patient initially arrives at the location of one of subscribing providers 10 and fills out the usual paperwork. This paperwork will include a consent form whereby the patient gives consent for this provider to provide to other providers health documents pertaining to that particular patient. This patient's consent may be a limited to only a) certain types of documents, b) certain types of requesting providers (e.g., hospitals) and/or c) certain specific providers.

The provider thereupon transmits a registration message (503) to health information exchange 20 identifying itself and providing information identifying the patient including the patient's personal and demographic information and consent choices, any or all of which can be later updated by transmitting an appropriate message to health information exchange 20.

Figure 3:
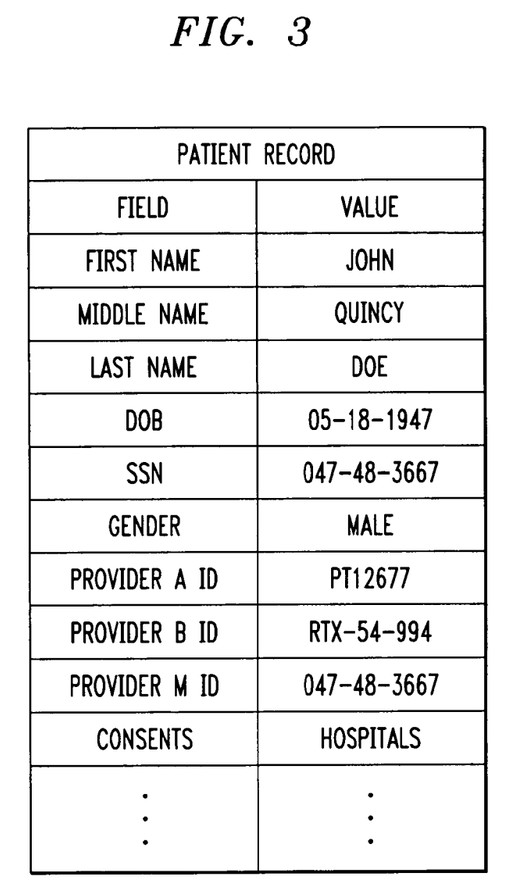
FIG. 3 shows a typical patient record maintained by the health information exchange.

As indicated at 505, health information exchange 20 thereupon consults RLS/PIX manager 221 to determine if the patient is already known to health information exchange 20, as would be the case if the patient had already been registered at another provider. If the patient is not known, the patient's name, other personal information and his/her demographic information is entered into RLS/PIX manager 221 at 508. Whether or not the patient was previously registered at a different provider, the above-mentioned identifier by which the patient is identified at the provider in question, per FIG. 3, is also entered, as indicated at 510. In this way the patient's identifying information is stored in association with an identification of said each one of the providers' electronic medical record systems. Health information exchange 20 thereupon confirms to the provider at 511 that the patient is now registered.

The workflow of FIG. 6 is an illustrative process by which health information exchange 20 services a request from a subscribing provider.

The process as depicted begins at 611 when health information exchange 20 receives a request from a requesting provider for a list of health documents pertaining to the patient in question. The requester's request may be as broad or as narrow as the requester may wish, specifying (or not, as the requester may choose) such criteria as the type of the document(s) sought, their date(s), the document source(s), etc. Although not shown in FIG. 6, health information exchange 20 confirms before proceeding that the requester is, in fact, one of the subscribing providers 10. If it is not, the subscriber may be offered the opportunity to become a subscriber. (This interchange is typically carried out via web portal 212, that being in all likelihood the mechanism via which the request was made.)

Assuming that the requester is a subscribing provider, health information exchange 20 determines at 612 whether the patient is registered with health information exchange 20 as being a patient of that provider. If not, then the requester is prompted to register the patient, per the process of FIG. 5.

Health information exchange 20 thereupon proceeds to compile a list of documents by querying various sources based on the criteria specified by the requester. One of those sources is document registries 235, as indicated at 617, and another is conventional health information exchanges 12, as indicated at 621.

In accordance with the principles of the present invention, health information exchange 20 further makes direct access queries to subscribing providers where the patient is registered, as indicated at 623.

Responsive to the queries from health information exchange 20, the queried entities each provide a list of documents that meet the requester's criteria and are consonant with policies that the provider may have in place that may restrict the health documents that it is willing to share to particular kinds of documents, particular types of requesters and/or particular requesters. The provider may also restrict the list to particular documents (or none) based on the consents given by the patient, or the provider may rely on health information exchange 20 to carry out this function.

Health information exchange 20 determines at 624 whether any documents are available to satisfy the request. There may be none either because none of the queried entities has any to share, and/or because health information exchange 20 determines that the patient has not consented to same. If no documents are available, health information exchange 20 so notifies the requester, as indicated at 626. Otherwise, as indicated at 628, health information exchange 20 provides to the requester a document list that is a compilation of the lists obtained at 617, 621 and 623. In compiling the compiled list, health information exchange 20 deletes any duplicate entries. Moreover, to the extent that a particular type of document is being requested, such as a CCD, only the most recent CCD available from a particular provider is listed. Thus the document list provided to the requester may include be all, or only a portion, of the list(s) received from the queried entities.

As indicated at 631, health information exchange 20 thereupon receives a message from the requester indicating which particular document(s) on the compiled list are desired. Health information exchange 20 thereupon obtains the documents from the appropriate source and transmits them to the requesting provider, as indicated at 632. Health information exchange 20 also stores the retrieved health documents to document repositories 235 so that it now has immediate access to these documents should additional requests be made.

Health information exchange 20 is also capable of mediating referral requests between providers. In this scenario a first one of providers 10 ("referring provider") wishes to refer one of its patients to another one of providers 10 ("referral provider"). For example, a psychiatrist's office wishes to refer one of its patients to an inpatient mental health facility.

FIG. 7 shows an illustrative referral process, which begins at 701 when health information exchange 20 receives a referral request from the referring provider. The referral request identifies the patient and indicates such criteria as the type of diagnosis, the type of facility sought to be referred to, geographic requirements and/or other criteria desired by the referring provider to be met by the referral provider. Health information exchange 20 confirms before proceeding, as before, that the referring provider is, in fact, one of the subscribing providers 10 and if not makes that opportunity available.

Health information exchange 20 then determines if the patient is registered, as indicated at 702. If not, it offers the referring provider the opportunity to register the patient. If the patient is already registered, or becomes registered at this time, health information exchange 20 then consults its list of providers in administrative tools/data 238 and determines at 704 whether there are any providers that meet the stated criteria. If not, the referring provider is so notified, as indicated at 706. Otherwise, a list of matching providers is sent to the referring provider, as indicated at 707.

The referring provider—either by human interaction via web interface 413 or automatically by its electronic medical record system—thereupon selects one of the referral providers from the list and identifies it to health information exchange 20. Upon receiving the selection at 708, health information exchange 20 transmits a message to the selected referral provider at 711 indicating that the referring provider wishes to make the referral. This message includes some or all of the information from the original referral request.

Health information exchange 20 thereupon notes internally, per the "long running business transaction" message processing scenario mentioned earlier, that it is waiting for a response from the selected referral provider's electronic medical record system confirming that it has received the referral. If, as indicated at 712, health information exchange 20 does not receive the confirmation, health information exchange 20 so notifies the referring provider at 714, after which, at 717, health information exchange 20 may receive from the referring provider an alternative choice selected from the list of matching providers that was sent at 707, at which point the process loops back to 711.

If, on the other hand, receipt of the referral is confirmed by the referral provider's electronic medical record system, health information exchange 20 notifies the referring provider's system of this fact at 716. At any time thereafter, as indicated at 722, requests for health documents pertaining to the patient may be received from the selected referral provider and those requests are responded to per the process of FIG. 6. By having received the referral, the referral provider knows to expect to be contacted by the patient. Thus if the patient does not make such contact, the referral provider is in a position to call the referring provider or take some other action. This is an especially common occurrence in the mental health field.

Figure 9:
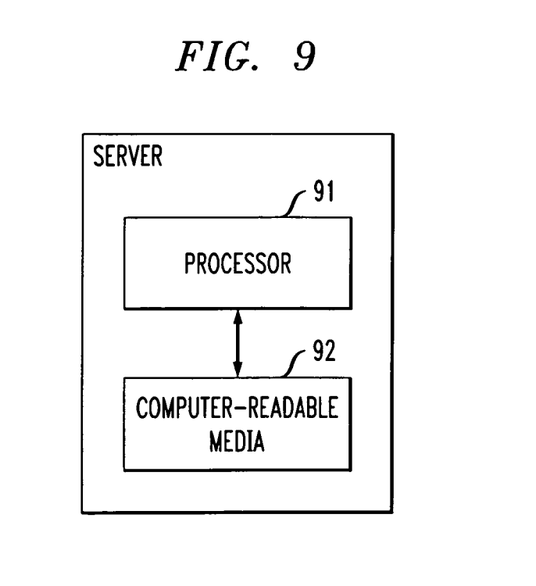
FIG. 9 shows an overall block diagram of the server that illustratively implements the health information exchange.

FIG. 9 shows that the server that illustratively implements health information exchange 20 includes a processor 91 and one or more computer-readable media 92. The server also includes other conventional elements (not shown) that those skilled in the art will recognize as being deemed desirable to implement the functionalities of health information exchange 20 as described herein. Stored on media 92 are machine-readable instructions that, when executed by processor 91, cause the functionalities of health information exchange to be implemented, including causing the health information exchange to transmit outgoing messages, and to receive incoming messages, as described herein.

The foregoing merely illustrates the principles of the invention. Those skilled in the art will be able to devise numerous alternative methods and arrangements which, while not shown or described herein, embody the principles of the invention and thus are within their spirit and scope.

What is claimed and desired to be secured by Letters Patent is as follows:

1. A data processing system installed behind a firewall located within a local provider network, comprising:
    a first interface capable of exchanging a first plurality of internet protocol (IP) data packets over the Internet with a first server of a health information exchange located remote from the local provider network, wherein the first plurality of IP data packets each include a data payload portion in which data is formatted in accordance with a first messaging protocol comprising one or a combination of Health Level Seven Version 2.x, Health Level Seven Version 3, and IHE (Integrating the Health Enterprise) Technical Framework;
    a second interface capable of exchanging a second plurality of IP data packets with a second server of an electronic medical record system located within the local provider network, wherein the second plurality of IP data packets each include a data payload portion in which data is formatted in accordance a second messaging protocol comprising one or a combination of Health Level Seven Version 2.x, Health Level Seven Version 3, and IHE (Integrating the Health Enterprise) Technical Framework that is different from the first messaging protocol; and
    a translator capable of (a) receiving the first plurality of IP data packets from the first interface, translating the format of the data payload portion of the first plurality of IP data packets from the format of the first messaging protocol to the format of the second messaging protocol, and transmitting the translated IP data packets to the second interface and (b) receiving the second plurality of IP data packets from the second interface, translating the format of the data payload portion of the second plurality of IP data packets from the format of the second messaging protocol to the format of the first messaging protocol, and transmitting the translated IP data packets to the first interface;
    wherein the first interface, the second interface, and the translator are each installed behind a firewall within the local provider network.

2. The data processing system of claim 1, wherein each of the first and second messaging protocols comprises an ISO level 7 (application layer) protocol.

3. The data processing system of claim 1, wherein each of the first and second messaging protocols defines a plurality of fields within the data payload portion of the IP data packets.

4. The data processing system of claim 1, wherein the second interface comprises a database interface that enables the second interface to directly access a database management system located within the local provider network and retrieve information from the database management system in response to a database query within the data payload portion of the first plurality of IP data packets.

5. The data processing system of claim 1, wherein the second interface comprises a web interface that enables the second interface to communicate with users via a web browser.

6. A data processing system located within a local provider network, comprising:
   a first interface capable of exchanging a first plurality of internet protocol (IP) data packets over the Internet with a first server of a health information exchange located remote from the local provider network, wherein the first plurality of IP data packets each include a data payload portion in which data is formatted in accordance with a first messaging protocol;
   a second interface capable of exchanging a second plurality of IP data packets with a second server of an electronic medical record system located within the local provider network, wherein the second plurality of IP data packets each include a data payload portion in which data is formatted in accordance a second messaging protocol that is different from the first messaging protocol; and
   a translator capable of (a) receiving the first plurality of IP data packets from the first interface, translating the format of the data payload portion of the first plurality of IP data packets from the format of the first messaging protocol to the format of the second messaging protocol, and transmitting the translated IP data packets to the second interface and (b) receiving the second plurality of IP data packets from the second interface, translating the format of the data payload portion of the second plurality of IP data packets from the format of the second messaging protocol to the format of the first messaging protocol, and transmitting the translated IP data packets to the first interface;
   wherein the first interface, the second interface, and the translator are each installed behind a firewall within the local provider network.

7. The data processing system of claim 6, wherein each of the first and second messaging protocols comprises an ISO level 7 (application layer) protocol.

8. The data processing system of claim 6, wherein each of the first and second messaging protocols defines a plurality of fields within the data payload portion of the IP data packets.

9. The data processing system of claim 6, wherein the second interface comprises a database interface that enables the second interface to directly access a database management system located within the local provider network and retrieve information from the database management system in response to a database query within the data payload portion of the first plurality of IP data packets.

10. The data processing system of claim 6, wherein the second interface comprises a web interface that enables the second interface to communicate with users via a web browser.

11. A data processing system located within a local provider network, comprising:
    a first interface capable of exchanging a first plurality of internet protocol (IP) data packets over the Internet with a first server of a health information exchange located remote from the local provider network, wherein the first plurality of IP data packets each include a data payload portion in which data is formatted in accordance with a first messaging protocol comprising one or a combination of Health Level Seven Version 2.x, Health Level Seven Version 3, and IHE (Integrating the Health Enterprise) Technical Framework;
    a second interface capable of exchanging a second plurality of IP data packets with a second server of an electronic medical record system located within the local provider network, wherein the second plurality of IP data packets each include a data payload portion in which data is formatted in accordance a second messaging protocol comprising one or a combination of Health Level Seven Version 2.x, Health Level Seven Version 3, and IHE (Integrating the Health Enterprise) Technical Framework that is different from the first messaging protocol, wherein the second interface is capable of directly accessing a database management system located within the local provider network and retrieving information from the database management system in response to a database query within the data payload portion of the first plurality of IP data packets; and
    a translator capable of (a) receiving the first plurality of IP data packets from the first interface, translating the format of the data payload portion of the first plurality of IP data packets from the format of the first messaging protocol to the format of the second messaging protocol, and transmitting the translated IP data packets to the second interface and (b) receiving the second plurality of IP data packets from the second interface, translating the format of the data payload portion of the second plurality of IP data packets from the format of the second messaging protocol to the format of the first messaging protocol, and transmitting the translated IP data packets to the first interface;
    wherein the first interface, the second interface, and the translator are each installed behind a firewall within the local provider network.

12. The data processing system of claim 11, wherein each of the first and second messaging protocols comprises an ISO level 7 (application layer) protocol.

13. The data processing system of claim 11, wherein each of the first and second messaging protocols defines a plurality of fields within the data payload portion of the IP data packets.

14. The data processing system of claim 1, wherein the second interface comprises a web interface that enables the second interface to communicate with users via a web browser.

* * * * *

UNITED STATES PATENT AND TRADEMARK OFFICE
CERTIFICATE OF CORRECTION

PATENT NO. : 10,530,901 B1
APPLICATION NO. : 14/990454
DATED : January 7, 2020
INVENTOR(S) : Matthew Arnheiter and Michael Brand It is certified that error appears in the above-identified patent and that said Letters Patent is hereby corrected as shown below:

In the Claims

Column 16
Lines 25 and 26, Claim 1, delete "installed behind a firewall" between "system" and "located".

Signed and Sealed this
Seventh Day of April, 2020

Andrei Iancu
*Director of the United States Patent and Trademark Office*